(12) United States Patent
Kim et al.

(10) Patent No.: US 10,912,659 B2
(45) Date of Patent: Feb. 9, 2021

(54) ORTHOPEDIC DEVICE AND POLYMER COMPOSITIONS FOR MAKING SAME

(71) Applicant: Ticona LLC, Florence, KY (US)

(72) Inventors: Sung Hye Kim, Erlanger, KY (US); Lowell Jay Larson, Independence, KY (US); Mark Allen Tyler, New Richmond, OH (US); Rong Luo, Florence, KY (US)

(73) Assignee: Ticona LLC, Florence, KY (US)

( * ) Notice: Subject to any disclaimer, the term of this patent is extended or adjusted under 35 U.S.C. 154(b) by 0 days.

(21) Appl. No.: 16/233,699

(22) Filed: Dec. 27, 2018

(65) Prior Publication Data

US 2019/0125548 A1 May 2, 2019

Related U.S. Application Data

(62) Division of application No. 15/452,824, filed on Mar. 8, 2017, now Pat. No. 10,166,120.

(Continued)

(51) Int. Cl.
| | |
|---|---|
| *A61F 2/02* | (2006.01) |
| *A61F 2/36* | (2006.01) |
| *A61F 2/38* | (2006.01) |
| *C08L 59/02* | (2006.01) |
| *C08L 59/04* | (2006.01) |
| *C08K 3/10* | (2018.01) |
| *C08K 5/10* | (2006.01) |
| *C08K 5/16* | (2006.01) |

(Continued)

(52) U.S. Cl.
CPC .............. *A61F 2/4684* (2013.01); *A61F 2/36* (2013.01); *A61L 27/26* (2013.01); *C08L 59/02* (2013.01); *C08L 59/04* (2013.01); *A61F 2/389* (2013.01); *A61F 2002/30616* (2013.01); *A61F 2310/00005* (2013.01); *A61L 2430/02* (2013.01); *A61L 2430/24* (2013.01)

(58) Field of Classification Search
None
See application file for complete search history.

(56) References Cited

U.S. PATENT DOCUMENTS

| | | | | |
|---|---|---|---|---|
| 4,608,052 A | * | 8/1986 | Van Kampen | A61F 2/30771 623/23.29 |
| 4,843,115 A | | 6/1989 | Auerbach et al. | |

(Continued)

FOREIGN PATENT DOCUMENTS

EP          0179668          4/1986

OTHER PUBLICATIONS

International Search Report and Written Opinion PCT/US17/21249, dated May 31, 2017, 24 pages.

(Continued)

*Primary Examiner* — Tae H Yoon
(74) *Attorney, Agent, or Firm* — Dority & Manning, P.A.

(57) ABSTRACT

Orthopedic devices are described including polymer compositions used to make the devices. The polymer composition contains a polyoxymethylene polymer in combination with various additives that prevent against agglomerations and spotting even when the composition contains significant amounts of coloring agents and/or waxes. In addition, the polymer composition has reduced formaldehyde emissions and excellent thermal stability properties.

14 Claims, 6 Drawing Sheets

Related U.S. Application Data

(60) Provisional application No. 62/305,032, filed on Mar. 8, 2016.

(51) Int. Cl.
*A61F 2/46* (2006.01)
*A61L 27/26* (2006.01)
*A61F 2/30* (2006.01)

(56) References Cited

U.S. PATENT DOCUMENTS

| | | |
|---|---|---|
| 5,973,081 A | 10/1999 | Kanai et al. |
| 6,512,047 B2 | 1/2003 | Kim et al. |
| 6,558,428 B2 | 5/2003 | Park |
| 6,716,248 B2 | 4/2004 | Huene |
| 6,974,849 B2 | 12/2005 | Notorgiacomo |
| 7,906,594 B2 | 3/2011 | Muck et al. |
| 8,053,499 B2 | 11/2011 | Disch et al. |
| 9,090,770 B2 | 7/2015 | Horio et al. |
| 9,278,021 B2 * | 3/2016 | Weaver, II ............ A61F 5/32 |
| 9,301,845 B2 | 4/2016 | Bonutti |
| 10,166,120 B2 | 1/2019 | Kim et al. |
| 2007/0129484 A1 | 6/2007 | Horio |
| 2009/0143506 A1 | 6/2009 | Harashina |

OTHER PUBLICATIONS

Fleming Polymer Testing & Consultancy: Melt Mass flow rate/Melt volume-flow rate (Fleming); paragraph 4, 1 page.
Copolyamide (Rowak AG); p. 1, Paragraph 1 & p. 2, Paragraph 2, 2 pages.

* cited by examiner

ORTHOPEDIC DEVICE AND POLYMER COMPOSITIONS FOR MAKING SAME

RELATED APPLICATIONS

The present application is a divisional application of U.S. patent application Ser. No. 15/452,824, filed on Mar. 8, 2017, which issued as U.S. Pat. No. 10,166,120 and which is based on and claims priority to U.S. Provisional Patent Application Ser. No. 62/305,032, filed on Mar. 8, 2016, both of which are incorporated herein by reference.

BACKGROUND

Orthopedic devices are artificial devices used to replace or strengthen a particular part of the body. Such devices can be used in humans or animals to repair or replace diseased or damaged bone, allied tissue associated with the bone, and/or joints associated with the bone. Primarily, orthopedic devices are used to correct or prevent skeletal deformities or injuries and to alleviate the pain and discomfort associated with the deformities or injuries.

When implanting a prosthesis, typically a receiving site or cavity is first prepared in an adjoining bone. In particular, the bone can be cut and reamed out in order to accommodate the prosthesis. A bone cement is then mixed and placed in the receiving site or cavity. A prosthesis is positioned in the bone cement, and the bone cement is subsequently cured and hardened affixing the prosthesis to the bone.

Once implanted, an orthopedic device ideally closely assimilates the characteristics of the bone and/or the joint that the device is intended to repair or replace. The implanted orthopedic device should be capable of supporting and withstanding stresses and strains normally imparted to the repaired or replaced bone joints.

In the past, many orthopedic devices were made from metals, such as stainless steel, titanium, and cobalt chrome alloys. Metal devices, however, tend to be less flexible and more rigid than bone material. Thus, those skilled in the art have attempted to design orthopedic devices made from polymer materials that have physical properties more similar to the physical properties of bone. For instance, ultrahigh molecular weight polyethylene has been incorporated into orthopedic devices.

In the past, polyoxymethylene polymers have also been used to produce orthopedic devices including trial sizers for joint replacement parts such as for the hip and knee. When used as a trial sizer, the orthopedic device may be reused during different operations. At the end of each use, the orthopedic device may be steam sterilized. Unfortunately, various problems have been experienced with the polyoxymethylene polymer composition. For instance, prior polyoxymethylene polymer compositions have a tendency to generate agglomerates that adversely interfere with the appearance of the device, especially when the device is color coded. In addition, blooming has occurred on the polyoxymethylene polymer devices after multiple sterilizations, which appear as white spots on the surface of the device. In view of the above, a need exists for a polymer composition, and particularly a polyoxymethylene polymer composition, for producing orthopedic devices, including trial sizers.

SUMMARY

The present disclosure is generally directed to medical products and devices including orthopedic devices, prosthetic devices, and the like. The present disclosure is also directed to polymer compositions for producing the medical devices. In accordance with the present disclosure, the polymer composition is formulated so as to minimize the formation of surface defects on the medical devices, such as agglomerates and spotting.

In one embodiment, the present disclosure is directed to an orthopedic device that comprises a molded article. The article comprises a joint engaging member made from a polymer material. In accordance with the present disclosure, the polymer material comprises a polyoxymethylene polymer blended with a copolyamide, a dicyandiamide, or mixtures thereof. In one embodiment, for instance, the polymer material contains both a copolyamide and a dicyandiamide at a weight ratio of greater than about 2:1, such as from about 2:1 to about 20:1, such as from about 5:1 to about 10:1.

The orthopedic device may comprise a hip prosthesis. Alternatively, the orthopedic device may comprise a knee prosthesis.

In one embodiment, the present disclosure is directed to an orthopedic sizing kit that includes a plurality of orthopedic devices that each include a joint engaging member made from the polymer material described above. Each joint engaging member of each orthopedic device may have a different size than the remainder of the orthopedic devices. Each joint engaging member may also have a different color than the remainder of the joint engaging members of the orthopedic devices. The orthopedic sizing kit can be used to determine the correct size of an orthopedic device during surgery. Once the correct size is determined, an orthopedic device can be implanted into the patient. For example, in one embodiment, the kit may include a second plurality of orthopedic devices wherein each of the orthopedic devices in the second plurality corresponds to and has the same size as one of the orthopedic devices in the first plurality. During an operation, the first plurality of orthopedic devices may be used to determine the appropriate size. One of the orthopedic devices from the second plurality is then selected and implanted into the patient. The orthopedic device implanted into the patient may have a joint engaging member that is comprised of an ultrahigh molecular weight polyethylene.

The present disclosure is also directed to a polymer composition. The polymer composition comprises a polyoxymethylene polymer. In one embodiment, the polyoxymethylene polymer may have a relatively low melt volume flow rate. For instance, the polyoxymethylene polymer may have a melt volume flow rate of less than about 20 cm$^3$/10 min, such as less than about 15 cm$^3$/10 min, such as less than about 10 cm$^3$/10 min, such as less than about 7 cm$^3$/10 min, such as less than about 5 cm$^3$/10 min, such as less than about 3 cm$^3$/10 min. In one embodiment, the melt volume flow rate of the polyoxymethylene polymer may be from about 1 cm$^3$/10 min to about 3.5 cm$^3$/10 min. The melt volume flow rate can be measured at 190° C. under a load 2.16 kg. The polyoxymethylene polymer may be present in the polymer composition in an amount of at least 70% by weight.

In accordance with the present disclosure, the polymer composition may further contain a copolyamide and a dicyandiamide blended with the polyoxymethylene polymer. The copolyamide and the dicyandiamide may be present in the composition at a weight ratio of greater than about 2:1.

In various embodiments, the polymer composition may further contain an acid scavenger. The acid scavenger, for instance, may comprise tricalcium citrate present in the composition in an amount from about 0.01% to about 0.1% by weight. The polymer composition may also contain one or more coloring agents in an amount greater than about 0.8% by weight. The coloring agent may comprise, for instance, titanium dioxide, a blue pigment, a yellow pigment, an orange pigment, or the like, and mixtures thereof. In one embodiment, the composition may be free of any coloring agents and have a natural color.

The polymer composition may also contain a phenolic antioxidant. The phenolic antioxidant may comprise hexamethylene glycol bis[3-(3,5-di-tert-butyl-4-hydroxyphenylpropionate)].

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which.

Figure 1:
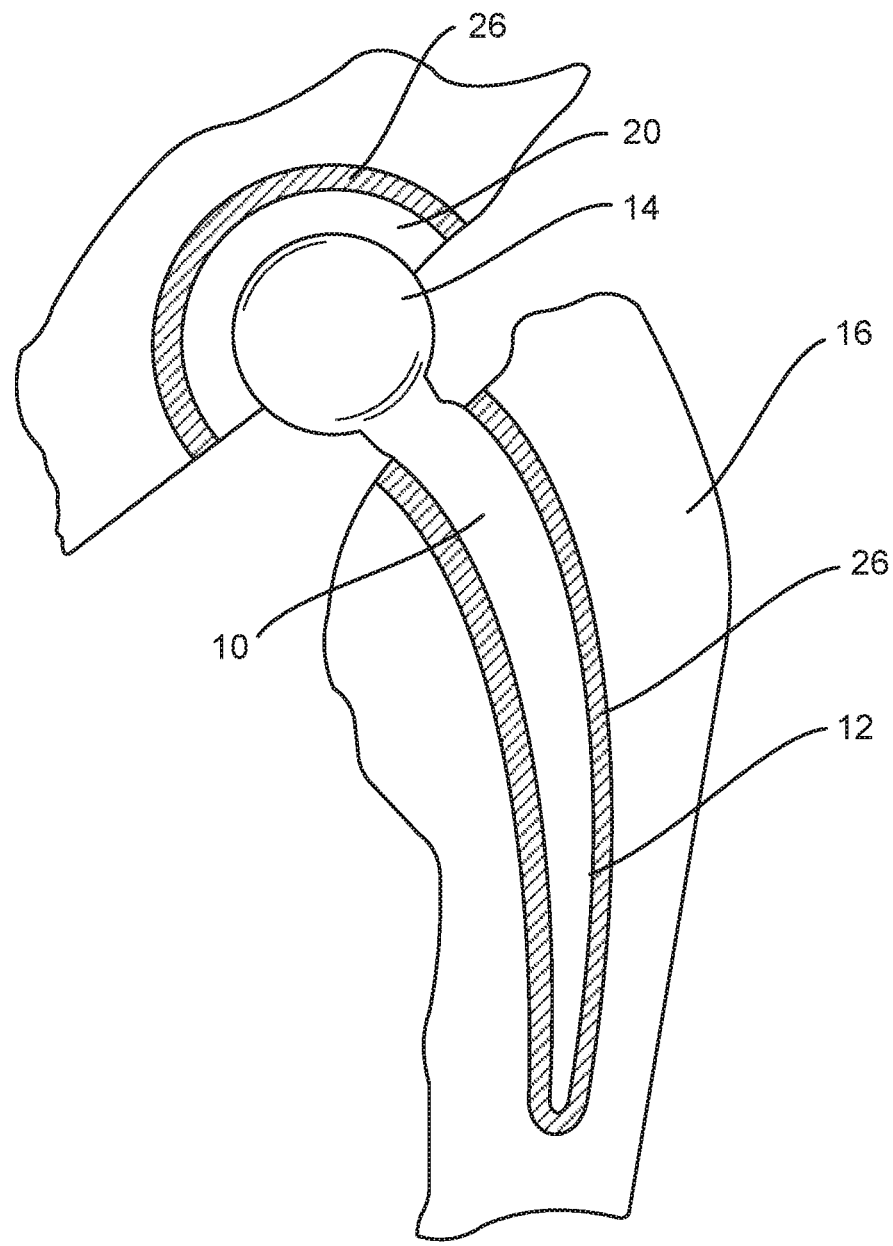
FIG. 1 is a cross-sectional view of an orthopedic device implanted into a bone.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to orthopedic devices, an orthopedic sizing kit, and to a polymer composition that may be used to produce the orthopedic devices. The polymer composition of the present disclosure is formulated to have a desired combination of physical properties. In addition, the polymer composition prevents against polymer blooming on the surface of the molded articles, even after a steam sterilization cycle. The polymer composition also prevents against the formation of agglomerates that can not only result in non-uniform properties but can also produce surface defects. The polymer composition of the present disclosure can also possess excellent thermal stability characteristics.

In general, the polymer composition of the present disclosure contains a polyoxymethylene polymer combined with a copolyamide, a dicyandiamide, or mixtures thereof. In addition, the polymer composition can contain an acid scavenger and a phenolic antioxidant. Of particular advantage, the polymer composition can contain relatively high amounts of colorants for color coding molded articles made from the composition. For instance, the polymer composition can contain one or more coloring agents in an amount greater than about 0.5% by weight, such as in an amount greater than about 0.8% by weight, such as in an amount greater than about 1% by weight. In an alternative embodiment, the polymer composition may have a natural color and not contain any coloring agents.

The polymer composition may be used to form all different types of molded articles and may be used in a wide variety of applications. The polymer composition is particularly well suited for use in producing medical devices and medical products. For instance, in one embodiment, the polymer composition can be used to produce an orthopedic device, such as a hip prosthesis or a knee prosthesis. The polymer composition, for instance, is capable of being used in any suitable medical application and is particularly well suited for load bearing joint implants.

Referring to FIG. 1, for instance, a hip implant is illustrated. The hip implant includes a hip prosthesis 10 having a stem 12 and a joint engaging member or head 14. The hip prosthesis 10 can be made from a polymer material in accordance with the present disclosure. As shown, the hip prosthesis 10 has been inserted into a cavity reamed into a bone 16, such as a femur.

The hip implant illustrated in FIG. 1 further includes an acetabular cup 20 that can also be made in accordance with the present disclosure. Acetabular cup 20 comprises a joint engaging member that is adapted to receive the head 14 of the hip prosthesis 10.

In order to implant the hip prosthesis 10 and the acetabular cup 20, both articles can be cemented to the bone using a bone cement 26.

In addition to being used to produce hip implants, the polymer composition of the present disclosure can also produce various other orthopedic devices. For instance, the polymer composition is well suited to producing a knee prosthesis, including a tibia plateau.

In one embodiment, the polymer composition is used to produce trial sizers that assist a physician or surgeon with determining the correct size of an implant during an operation. In one embodiment, each of the trial sizers may be color coded in order to indicate a particular size.

Figure 2:
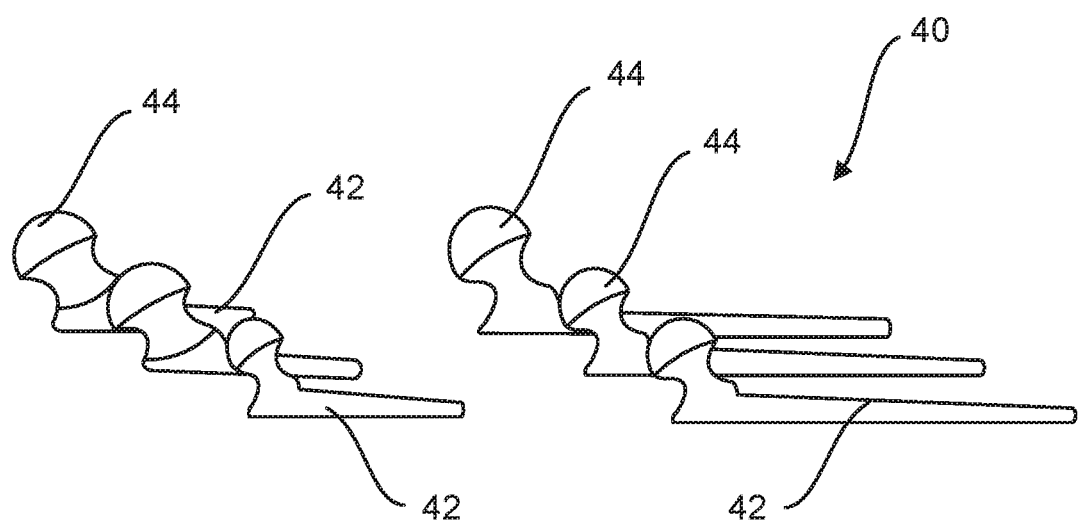
FIG. 2 is a perspective view of orthopedic devices that may be made in accordance with the present disclosure.

For instance, referring to FIG. 2, a plurality of orthopedic devices 40 are shown. The plurality of orthopedic devices 40 can all be made from the polymer composition of the present disclosure. As shown, each orthopedic device 40 includes a stem 42 and a joint engaging member or head 44. The entire orthopedic device can be made from the polymer composition or, alternatively, only the head or joint engaging member may be made from the polymer composition of the present disclosure. In yet another embodiment, the polymer composition may comprise a coating that is used to produce the joint engaging member.

As shown in FIG. 2, each orthopedic device 40 has a different dimension or size and, as described above, can each be produced with a different color. During a surgical operation, a bone site can be prepared for insertion of the implant. The plurality of orthopedic devices 40 as shown in FIG. 2 can then be used by the surgeon to determine the proper size of the prosthesis that should be used on the particular patient. Once the appropriate size is determined, the surgeon can select an orthopedic device from a second plurality of devices that is to be inserted into the body of the patient. The second plurality of orthopedic devices can be made from the same polymer composition or can be made from a different material. For instance, in one embodiment, the second plurality of orthopedic devices can be made from a different polymer, such as an ultrahigh molecular weight polyethylene. In another embodiment, the orthopedic device to be inserted into the patient may be made from a metal, such as stainless steel or titanium.

In one embodiment, the polymer composition of the present disclosure comprises a polyoxymethylene polymer in combination with a copolyamide and a dicyandiamide. In addition, the polymer composition may contain one or more coloring agents. The copolyamide and the dicyandiamide are combined with the polyoxymethylene polymer in a manner so that the generation of agglomerates and spotting on the surface of molded articles made from the composition are minimized. For example, in one embodiment, the copolyamide and the dicyandiamide are present in the composition at a weight ratio of greater than about 2:1. The weight ratio between the copolyamide and the dicyandiamide, for instance, can be from about 2:1 to about 20:1, such as from about 5:1 to about 10:1. In addition to dramatically improving the appearance of molded articles made from the polymer composition by preventing agglomerates and spotting, the copolyamide and dicyandiamide also serve to prevent formaldehyde release from the composition and significantly improve thermal stability. In one embodiment, the above additives have been found to completely eliminate blooming on the surface of a molded article made in accordance with the present disclosure even after repeated steam sterilization cycles, such as even after 50 cycles of steam sterilization. The polymer composition also shows no cytotoxic reactivity.

The polyoxymethylene polymer may comprise any suitable homopolymer or copolymer of polyoxymethylene. Polyoxymethylenes are generally unbranched linear polymers that may contain at least 80%, such as at least 90% oxymethylene units (—$CH_2$—O—). The homopolymers are generally obtained by polymerizing formaldehyde or trioxane, wherein the polymerization is initiated cationically or anionically. Copolymers of polyoxymethylenes may contain not only oxymethylene units but also oxyalkylene units, where the alkylene groups may contain from about 2 to about 8 carbon units, linear or branched. The term polyoxymethylenes as used herein encompasses homopolymers of formaldehyde or its cyclic oligomers, such as trioxane or tetroxane, and also corresponding copolymers.

Homopolymers of formaldehyde or of trioxane are polymers whose hydroxy end groups have been chemically stabilized in a known manner with respect to degradation, e.g. via esterification or via etherification. Copolymers are polymers composed of formaldehyde or of its cyclic oligomers, in particular trioxane, and of cyclic ethers, of cyclic acetals, and/or of linear polyacetals.

Very generally, these polymers have at least 50 mol % $CH_2$—O— repeat units in the main polymer chain. The homopolymers are generally prepared via polymerization of formaldehyde or trioxane, preferably in the presence of suitable catalysts.

POM copolymers are generally preferred in the molding compositions, particularly those which also contain, besides the —$CH_2$—O— repeat units, up to 50 mol %, preferably from 0.1 to 20 mol %, and in particular from 0.5 to 10 mol %, of —O—$R^1$— repeat units, where $R^1$ is a saturated or ethylenically unsaturated alkylene group having at least two carbon atoms, or a cycloalkylene group, which, if appropriate, has sulfur atoms or preferably oxygen atoms in the chain, and which, if appropriate, bears one or more substituents selected from the group consisting of alkyl, cycloalkyl, aryl, aralkyl, heteroaryl, halogen, or alkoxy.

$R^1$ is preferably a $C_2$-$C_4$-alkylene group which, if appropriate, has one or more substituents which are $C_1$-$C_4$-alkyl groups, or are $C_1$-$C_4$-alkoxy groups, and/or are halogen atoms, preferably chlorine atoms, or a group of the formula —(($C_nH_{2n}$)—O—O—)$_m$, in which n is a whole number from 2 to 4 and m is 1 or 2.

These groups can advantageously be introduced into the copolymers via ring-opening of cyclic ethers and/or acetals.

Preferred cyclic ethers or acetals are those of the formula:

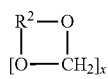

in which x is 0 or 1 and $R^2$ is a $C_2$-$C_4$-alkylene group or an alkyleneoxyalkylene unit which, if appropriate, have one or more substituents which are $C_1$-$C_4$-alkyl groups, or which are $C_1$-$C_4$-alkoxy groups, and/or which are halogen atoms, preferably chlorine atoms.

Merely by way of example, mention may be made of ethylene oxide, propylene 1,2-oxide, butylene 1,2-oxide, butylene 1,3-oxide, 1,3-dioxane, dioxolane, and 1,3-dioxepan as cyclic ethers, and also of linear oligo- or polyformals, such as polydioxolane or polydioxepan, as comonomers.

It is particularly advantageous to use copolymers composed of from 99.5 to 95 mol % of trioxane and of from 0.5 to 5 mol % of one of the above-mentioned comonomers.

Other polyoxymethylenes likewise suitable are oxymethylene terpolymers which by way of example are prepared via reaction of trioxane and of one of the cyclic ethers or acetals described above, and using a third monomer, preferably a bifunctional compound of the formula:

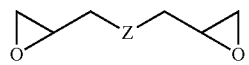

where Z is a chemical bond, —O—, or —O—$R^3$—O— ($R^3$=$C_2$-$C_8$-alkylene or $C_2$-$C_8$-cycloalkylene).

Preferred monomers of this type are ethylene diglycide, diglycidyl ether and diethers composed of glycidyl compounds and formaldehyde in a molar ratio of 2:1, and also diethers composed of 2 mol of glycidyl compound and 1 mol of an aliphatic diol having from 2 to 8 carbon atoms, examples being the diglycidyl ether of ethylene glycol, 1,4-butanediol, 1,3-butanediol, 1,3-cyclobutanediol, 1,2-propanediol, and 1,4-cyclohexanediol, and also diglycerol diformal, to mention just a few examples.

In one embodiment, the preparation of the polyoxymethylene can be carried out by polymerization of polyoxymethylene-forming monomers, such as trioxane or a mixture of trioxane and dioxolane, in the presence of ethylene glycol or methylal as a molecular weight regulator. The polymerization can be effected as precipitation polymerization or in the melt. Initiators which may be used are the compounds known per se, such as trifluoromethane sulfonic acid, these preferably being added as solution in ethylene glycol to the monomer. The catalyst can be a liquid, solid or gas. In one embodiment, the catalyst may comprise a boron compound, such as boron trifluroride. Boron trifluroride may be present during the processes of gas. The procedure and termination of the polymerization and working-up of the product obtained can be effected according to processes known per se. By a suitable choice of the polymerization parameters, such as duration of polymerization or amount of molecular weight regulator, the molecular weight and hence the MVR value of the resulting polymer can be adjusted.

The melting point of the polyoxymethylene polymer (or blend of polymers) can vary depending upon how the polymer is made, its molecular weight, and various other factors. In one embodiment, for instance, the melting point can be from about 150° C. to about 200° C. The weight average molecular weight of the polymer can vary from about 5000 to about 200,000, such as from about 7000 to about 150,000.

The molecular weights, characterized as melt volume rate (MVR), of the oxymethylene polymers according to the invention can be adjusted within certain ranges. Typical MVR values are from 0.1 to 100 cm$^3$/10 min, such as from 0.8 to 50 cm$^3$/10 min, measured according to EN ISO 1133 at 190° C. under a load of 2.16 kg. In one embodiment, the polyoxymethylene polymer has a relatively low melt volume flow rate. For instance, the polymer can have a melt volume flow rate of less than about 10 cm$^3$/10 min, such as less than about 7 cm$^3$/10 min, such as less than about 5 cm$^3$/10 min, such as less than about 3 cm$^3$/10 min. The melt volume flow rate is generally greater than about 0.5 cm$^3$/10 min, such as greater than 1 cm$^3$/10 min, such as greater than about 1.5 cm$^3$/10 min, such as greater than about 2 cm$^3$/10 min.

The polyoxymethylene polymer may be present in the polyoxymethylene polymer composition in an amount of at least 60 wt. %, such as at least 70 wt. %, such as at least 80 wt. %, such as at least 85 wt. %, such as at least 90 wt. %, such as at least 95 wt. %. In general, the polyoxymethylene polymer is present in an amount of less than about 100 wt. %, preferably less than about 99.5 wt. %, such as less than about 99 wt. %, such as less than about 98 wt. % wherein the weight is based on the total weight of the polyoxymethylene polymer composition.

In accordance with the present disclosure, the polyoxymethylene polymer is combined with a copolyamide, a dicyandiamide, or mixtures thereof. The copolyamide and the dicyandiamide may serve as formaldehyde scavengers which can react with formaldehyde. In addition, it was discovered that the combination of a copolyamide and a dicyandiamide can reduce agglomerates and surface spotting.

The copolyamide can have a softening point of generally greater than about 120° C., such as greater than about 130° C., such as greater than about 140° C., such as greater than about 150° C., such as greater than about 160° C., such as greater than about 170° C. The softening point of the copolyamide may be less than about 210° C., such as less than about 200° C., such as less than about 190° C., such as less than about 185° C. The copolyamide may have a melt viscosity at 230° C. of greater than about 7 Pa s, such as greater than about 8 Pa s, such as greater than about 9 Pa s. The melt viscosity is generally less than about 15 Pa s, such as less than about 14 Pa s, such as less than about 13 Pa s. In one embodiment, the copolyamide is ethanol soluble. In one embodiment, the copolyamide may comprise a polycondensation product of polymeric fatty acids with aliphatic diamines.

The copolyamide and dicyandiamide can be included in the composition in a ratio of from about greater than 2:1, respectively. For example the ratio of copolyamide to dicyandiamide may be from about 2:1 to about 20:1, such as from about 5:1 to about 10:1, such as about 7:1 to about 8:1, respectively.

In one embodiment, the copolyamide may be present in the polymer composition in an amount greater than about 0.1% by weight, such as in an amount greater than about 0.11% by weight, such as in an amount greater than about 0.12% by weight. The copolyamide is generally present in an amount less than about 1% by weight. The dicyandiamide, on the other hand, is generally present in an amount from about 0.001% to about 1% by weight. The dicyandiamide, for instance, can be present in the composition in an amount from about 0.01% to about 0.05% by weight.

In one embodiment, the polymer composition may also include an acid scavenger. The acid scavenger may comprise a carboxylic salt, such as a carboxylic salt of divalent metal ions, such as carboxylic salts of alkaline earth metals.

The metal carboxylic salt may be a carboxylic salt having one or more carboxylic functions, and may contain one or more metal ions. It is therefore also possible to use mixed salts, i.e. salts having more than one metal ion. It is likewise possible to use mixed salts which derive from two or more different carboxylic acids.

Examples of suitable carboxylic acids are succinic acid, citric acid, acetic acid, formic acid, propionic acid, butyric acid, valeric acid, adipic acid, tartaric acid, stearic acid, palmitic acid, and montanic acids.

Examples of suitable metal ions are magnesium, calcium, strontium, barium, zinc, and aluminum.

Examples of acid scavengers which may be used advantageously are calcium citrate and tricalcium citrate. The acid scavenger may be present in the polymer composition in an amount from about 0.001% to about 2% by weight. The acid scavenger is generally present in an amount less than about 1% by weight, such as in an amount less than about 0.5% by weight. In one embodiment, for instance, the acid scavenger may be present in the polymer composition in an amount from about 0.01% by weight to about 0.1% by weight, such as from about 0.01% by weight to about 0.07% by weight.

Still another additive that may be present in the composition is a sterically hindered phenol compound, which may serve as an antioxidant. Examples of such compounds, which are available commercially, are pentaerythrityl tetrakis[3-(3,5-di-tart-butyl-4-hydroxyphenyl)propionate] (Irganox 1010, BASF), triethylene glycol bis[3-(3-tert-butyl-4-hydroxy-5-methylphenyl)propionate] (Irganox 245, BASF), 3,3'-bis[3-(3,5-di-tert-butyl-4-hydroxyphenyl)propionohydrazide] (Irganox MD 1024, BASF), hexamethylene glycol bis[3-(3,5-di-tert-butyl-4-hydroxyphenyppropionate] (Irganox 259, BASF), and 3,5-di-tert-butyl-4-hydroxytoluene (Lowinox BHT, Chemtura). Preference is given to Irganox 259. The above compounds may be present in the composition in an amount less than about 2% by weight, such as in an amount from about 0.01% to about 1% by weight.

In one embodiment, the composition may also contain one or more lubricants. The lubricant may comprise a polymer wax composition. Lubricants that may be included in the composition include, for instance, N,N'-ethylene bisstearamide. Lubricants can generally be present in the polymer composition in an amount from about 0.01% to about 5% by weight. For instance, a lubricant can be present in an amount greater than about 0.1% by weight, such as in an amount from about 0.1% to about 1% by weight.

As described above, in one embodiment, the polymer composition may contain one or more coloring agents. Coloring agents can be added to the composition in order to color code medical products made from the composition. In general, any suitable coloring agent may be incorporated into the polymer composition. For instance, the coloring agent may comprise any suitable dye or pigment or combination thereof.

Dyes or pigments that can be used include inorganic pigments, e.g. titanium oxide, zinc oxide, zinc sulfide, ultramarine blue, cobalt blue, or any desired organic dyes or pigments, e.g. phthalocyanines, anthraquinones, azo dyes, or carbon black, either individually or as a mixture. In one embodiment, the polymer composition may contain a blue pigment, a yellow pigment, or an orange pigment.

In general, one or more coloring agents can be present in the polymer composition in an amount from about 0.01% to about 5% by weight, such as from about 0.1% to about 2% by weight.

In one particular embodiment, relatively large amounts of coloring agents may be incorporated into this composition. For example one or more coloring agents can be incorporated into the composition such that the total amount of coloring agents can be greater than about 0.8% by weight, such as greater than about 0.9% by weight, such as greater than about 1% by weight, such as greater than about 1.1% by weight, such as greater than about 1.2% by weight. The total amount of coloring agents present in the composition is generally less than about 5% by weight, such as less than about 4% by weight, such as less than about 3% by weight. In one embodiment, one or more coloring agents are incorporated into the composition in an amount from about 1.4% by weight to about 2% by weight.

In an alternative embodiment, the composition may be free of any coloring agents such as dyes and pigments. For instance, in one embodiment, the polymer composition may exhibit its natural color.

The present disclosure may be better understood with reference to the following example.

EXAMPLE

Various polymer compositions were made and tested for various properties. Table 1 below lists the polymer compositions that were formulated. The compositions were compounded on a 25 mm co-rotating twin-screw extruder and formed into standard test plagues.

The samples of table 1 were compounded on a 25 mm co-rotating twin-screw extruder. Various samples produced herein were tested for tensile modulus, yield stress and strain, and impact strength. Tensile and yield properties were tested according to ISO 527. Charpy notched impact strength was tested according to ISO 179. Izod notched impact strength was tested according to ISO 180. Melt volume rate was tested according to ISO 1133 at 190° C. and 2.16 kg load. Mold shrinkage was tested according to ISO 294. Density was tested according to ISO 1183. Water absorption was tested according to ISO 62. Flexural modulus was tested according to ISO 178. Melting point was tested according to ISO 3146. DTUL was tested according to ISO 75. CLTE was tested according to ISO 11359. All tests were conducted according to the most recent ISO standard as of the filing date of this application.

TABLE 1

| | Sample 1 | Sample 2 | Sample 3 | Sample 4 |
|---|---|---|---|---|
| POM (MVR 2.5 cm$^3$/10 min) | 97.30 | 97.55 | 97.58 | 97.72 |
| Ethylene bisstearamide | 0.25 | 0.20 | 0.20 | 0.20 |
| Hexamethylene bis[3-(3,5-di-tert-butyl-4-hydroxyphenyl)propionate] | 0.50 | 0.50 | 0.50 | 0.50 |
| El Sucon (Ethylene Copolymer, CaAcetate, Surlyn compatibilizer, Elvamide polyamide) | 0.45 | | | |
| Copolyamide | | 0.15 | 0.15 | |
| Tricalcium citrate | | 0.10 | 0.05 | 0.05 |
| Dicyandiamide | | | 0.02 | |
| Melamine | | | | 0.03 |
| Titanium oxide | 1.50 | 1.50 | 1.50 | 1.50 |

Figure 3:
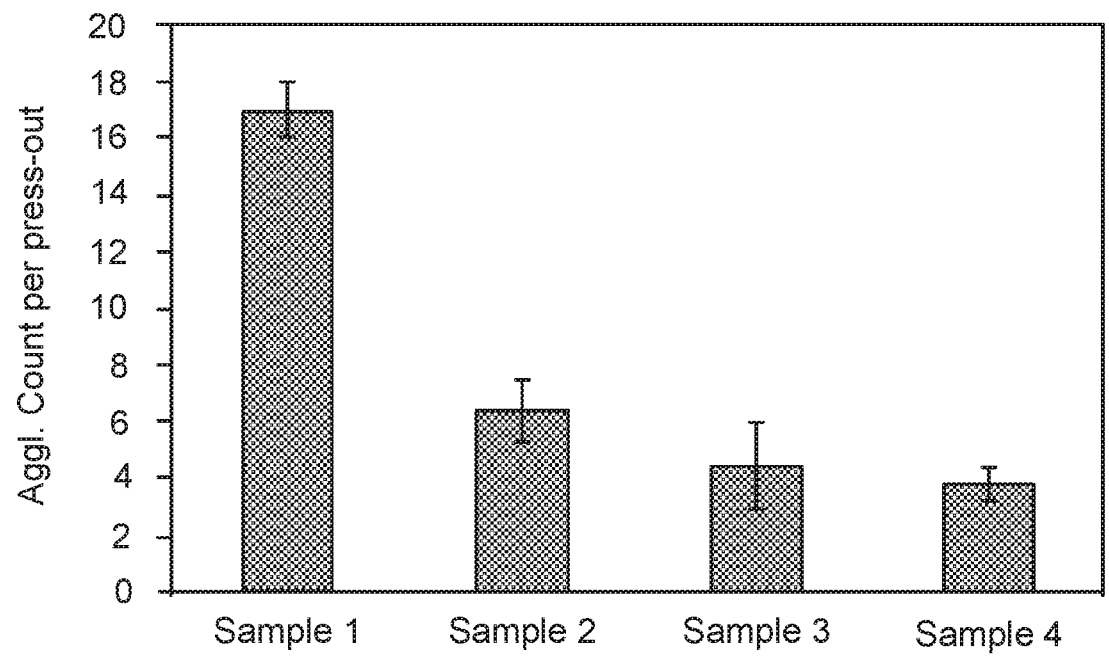
FIGS. 3 thru 9 are graphical representations of the results obtained in the example below.
Figure 4:
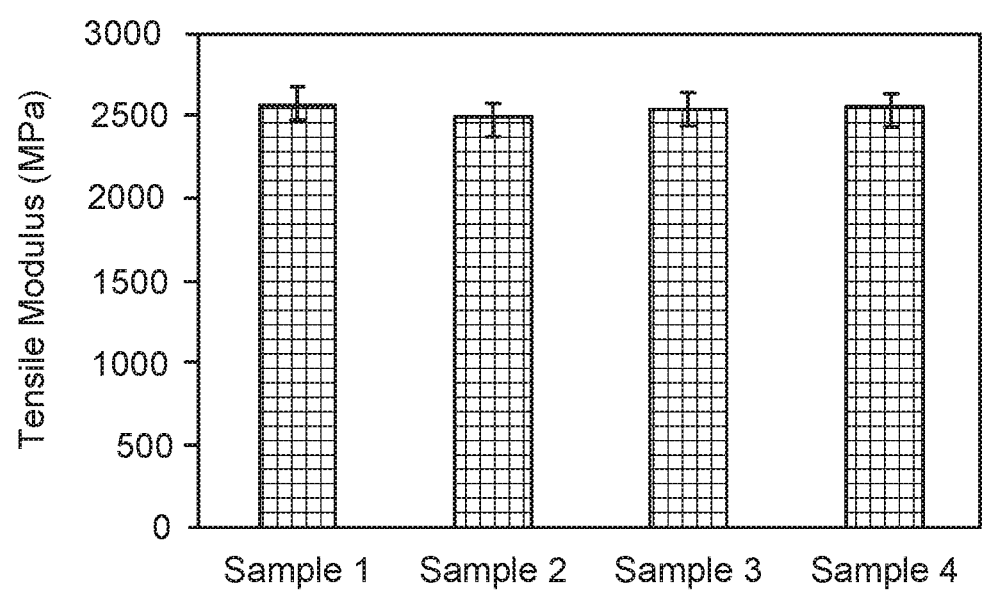
Figure 5:
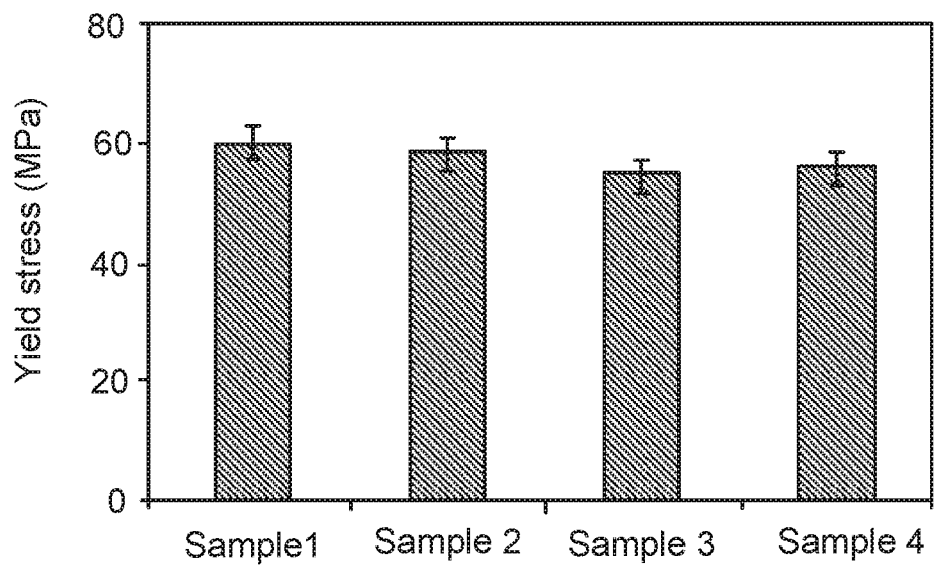
Figure 6:
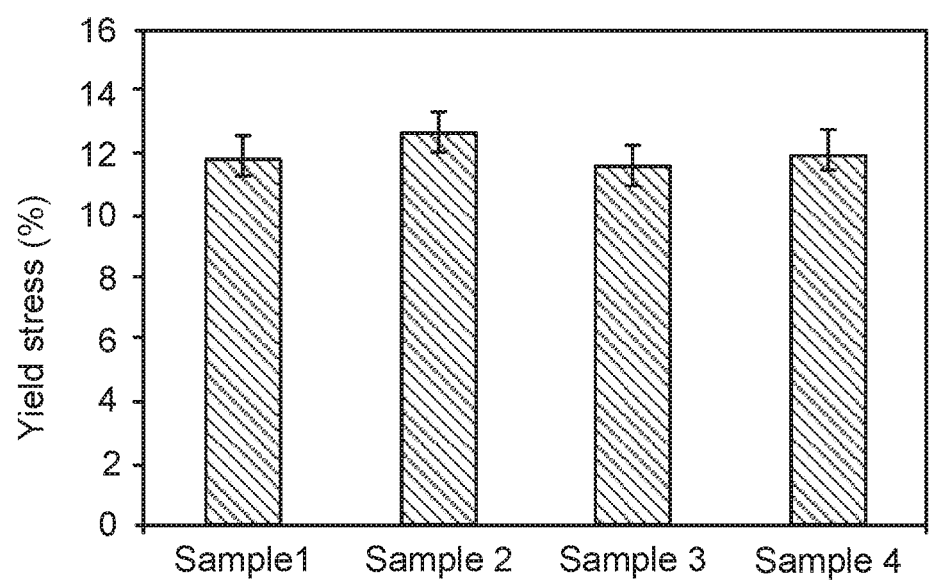
Figure 7:
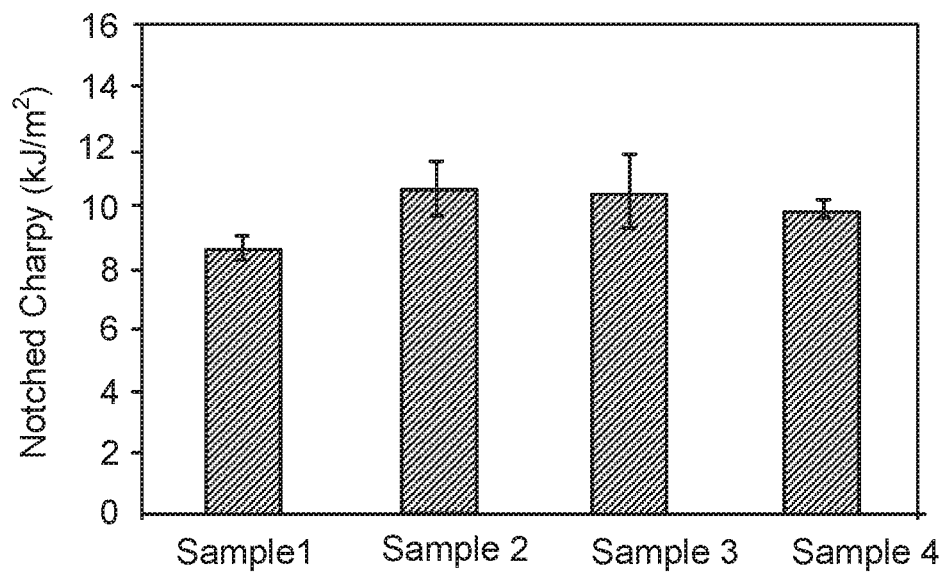

In addition to producing test plagues, the above formulations were also formed into pellets. In order to test for the formation of agglomerates, the pellets were hot-pressed. To prepare the press-out of each sample, 14 grams of pellets were melted under 1500 psi for 2 minutes and pressed under 10,000 psi for 1 minute on a hot-press set at 385° F. The press-outs were examined and the agglomerates were counted. The results are shown in FIG. 3. Three press-outs were quantified for each sample. As shown, Sample Nos. 2 thru 4 have significantly reduced agglomerates in comparison to Sample No. 1. Sample Nos. 2, 3 and 4, for instance, had greater than 60% less agglomerates than Sample No. 1.

The resultant samples were tested for tensile modulus, yield stress and strain, and impact strength. Tensile and yield properties were tested according to ISO 527. Charpy notched impact strength was tested according to ISO 179. All tests were conducted according to the ISO standards as of the filing date of this application. POM melt volume rate may be tested according to ISO 1133 at 190° C. and 2.16 kg load.

The results of the tensile test are shown in FIGS. 4 thru 7. As shown, all of the samples had similar physical properties. Sample Nos. 2 and 3, however, showed improved impact strength.

Figure 8:
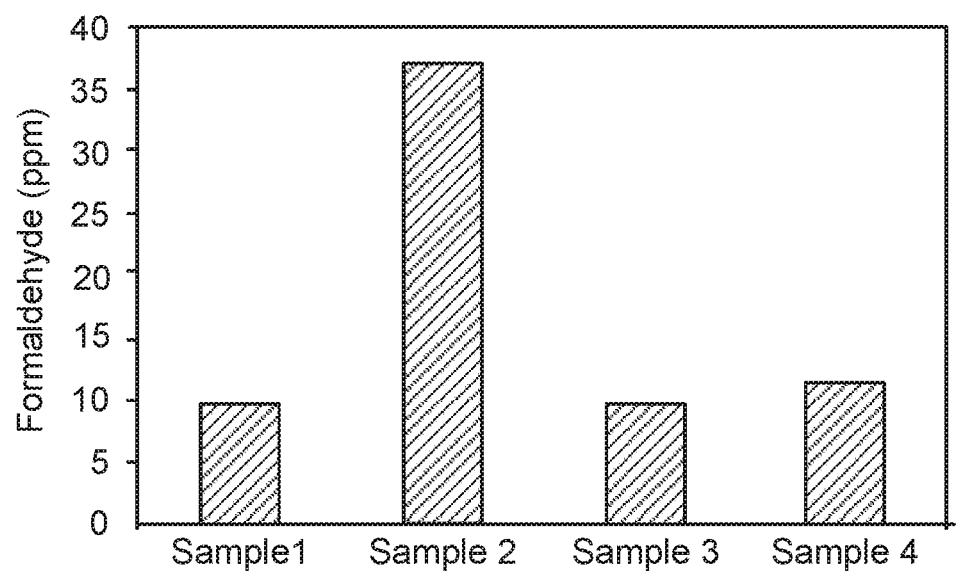
Figure 9:
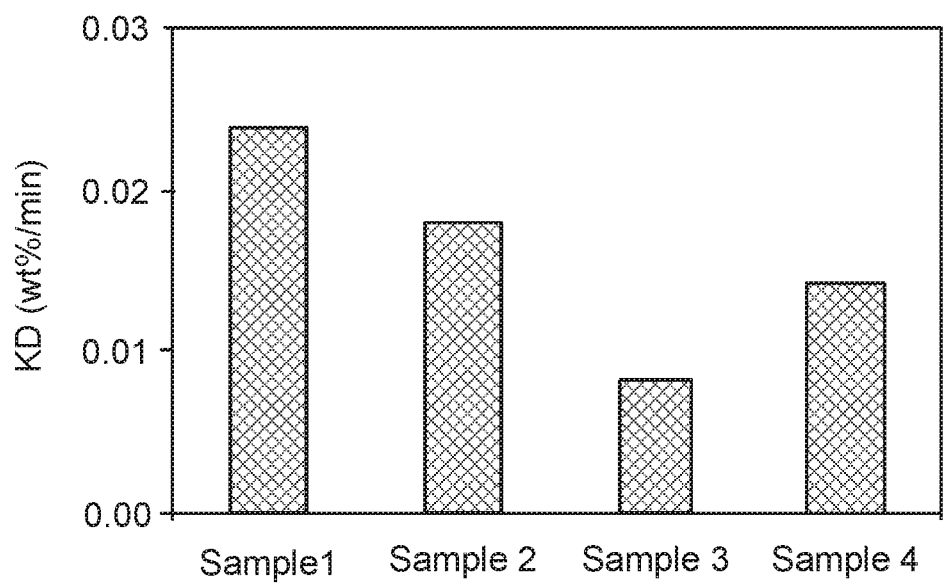

In order to produce orthopedic devices such as trial sizers, in one embodiment, the polymer composition of the present disclosure is combined with one or more coloring agents and extruded to form a rod. The rod is then machined into final shapes and dimensions. The extrusion process can be low shear but can be a lengthy process. Thus, polymer compositions according to the present disclosure should have robust thermal stability. Consequently, the formulations above were tested for thermal stability according to Test VDA275 (German Automotive Industry Recommendation No. 275) as documented by Kraftfahrwesen e. V., July 1994. The samples were also tested according to the $K_D$ Test. In the $K_D$ Test, the resin is heated at 230° C. for 30 minutes and the weight loss during this 30 minutes is recorded in weight percent per minute. The results are illustrated in FIGS. 8 and 9. As shown, Sample No. 3 demonstrated the best overall thermal stability.

Sample No. 3 as described above was then combined with different coloring agents and molded into test plagues. Three different formulations were produced. One formulation contained a yellow pigment, a second formulation contained an orange pigment, and a third formulation contained a blue pigment. The coloring agents were added to each composition in an amount of approximately 1.5% by weight. A 40 mm co-rotating twin-screw extruder was used to produce the test plagues.

The samples displayed the following properties:

TABLE 2

| | YELLOW | BLUE | ORANGE |
|---|---|---|---|
| Physical Properties | | | |
| Density, kg/m$^3$ | 1.416 | 1.416 | 1.411 |
| Melt Volume Rate, cm$^3$/10 min | 2.27 | 2.29 | 2.12 |
| Mold shrinkage - parallel, % | 2.36 | 3.03 | 2.79 |
| Mold shrinkage - normal, % | 1.82 | 1.61 | 1.62 |
| Water absorption (23° C.-sat), % | 0.39 | 0.40 | 0.41 |
| Mechanical Properties | | | |
| Tensile Modulus (1 mm/min), MPa | 2452 | 2650 | 2748 |
| Tensile Stress at yield (50 mm/min), MPa | 59.85 | 60.28 | 61.83 |
| Tensile Strain at yield (50 mm/min), % | 12.52 | 10.29 | 9.56 |
| Flexural modulus (23° C.), MPa | 2229 | 2260 | 2366 |
| Charpy impact strength @ 23° C., kJ/m$^2$ | No break | 148.9 | 226 |
| Charpy impact strength @ −30° C., kJ/m$^2$ | 7.0 | 4.9 | 5.6 |
| Charpy notched impact strength @ 23° C., kJ/m$^2$ | 8.9 | 5.7 | 6.7 |
| Izod notched impact strength @ 23° C., kJ/m$^2$ | 8.9 | 5.9 | 7.5 |

TABLE 2-continued

|  | YELLOW | BLUE | ORANGE |
|---|---|---|---|
| Thermal Properties | | | |
| Melting Temperature (10° C./min), ° C. | 166 | 164 | 167 |
| DTUL @ 1.8 Mpa, ° C. | 94 | 89 | 91 |
| CLTE - parallel, $10^{-4}/°$ C. | 1.4 | 1.4 | 1.4 |
| CLTE - normal, $10^{-4}/°$ C. | 1.4 | 1.4 | 1.2 |

The samples containing the yellow pigment were also found to pass a cytotoxicity test in addition to a sample having a natural color.

Tensile bars or test plagues obtained from the polymer composition containing the blue pigment were subjected to steam sterilization. Steam sterilization was performed under 21 psi pressure at 125 C for 35 minutes. The blue tensile bars were subjected to 50 cycles of steam sterilization and completely cooled down between each cycle. The test plagues did not show any evidence of spotting or blooming even after 50 cycles of steam sterilization. Further, the steam sterilized samples showed no degradation of mechanical properties when tested for tensile modulus and tensile stress at yield.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. An orthopedic device comprising:
   a molded article, the article comprising a joint engaging member made from a polymer material having a shape configured to be implanted into a patient, the polymer material comprising a polyoxymethylene polymer blended with a copolyamide and a dicyandiamide, the copolyamide and the dicyandiamide being present in the polymer material at a weight ratio of greater than 2:1, wherein the molded article is uncoated and made entirely from the polymer material.

2. An orthopedic device as defined in claim 1, wherein the copolyamide and the dicyandiamide are present in the polymer material at a weight ratio of from 2:1 to 20:1.

3. An orthopedic device as defined in claim 1, wherein the polymer material further comprises a coloring agent and an acid scavenger, the acid scavenger comprising tricalcium citrate.

4. An orthopedic device as defined in claim 1, wherein the polymer material further contains a phenolic antioxidant, the antioxidant comprising hexamethylene glycol bis[3-(3,5-di-tert-butyl-4-hydroxyphenylpropionate)].

5. An orthopedic device as defined in claim 1, wherein the orthopedic device comprises a hip prosthesis.

6. An orthopedic device as defined in claim 1, wherein the orthopedic device comprises a knee prosthesis.

7. An orthopedic sizing kit comprising:
   a plurality of orthopedic devices, each of the orthopedic devices including a joint engaging member made from a polymer material having a shape configured to be implanted into a patient, the polymer material comprising a polyoxymethylene polymer blended with a copolyimide and a dicyandiamide, each joint engaging member of each orthopedic device having a different size than the remainder of the orthopedic devices, each joint engaging member also having a different color than the remainder of the joint engaging members of the other orthopedic devices, the copolyamide and the dicyandiamide being present in the polymer material at a weight ratio of greater than 2:1, wherein each orthopedic device is uncoated and made entirely from the polymer material.

8. An orthopedic kit as defined in claim 7, wherein the copolyamide and the dicyandiamide are present in the polymer material at a weight ratio of from 2:1 to 20:1.

9. An orthopedic kit as defined in claim 7, wherein the polymer material further comprises a coloring agent and an acid scavenger, the acid scavenger comprising tricalcium citrate.

10. An orthopedic kit as defined in claim 7, wherein the polymer material further contains a phenolic antioxidant, the antioxidant comprising hexamethylene glycol bis[3-(3,5-di-tert-butyl-4-hydroxyphenylpropionate)].

11. An orthopedic kit as defined in claim 7, wherein the orthopedic devices comprise hip prostheses.

12. An orthopedic kit as defined in claim 7, wherein the orthopedic devices comprise knee prostheses.

13. An orthopedic kit as defined in claim 7, wherein the kit includes a second plurality of orthopedic devices each comprising a joint engaging member, each of the orthopedic devices in the second plurality corresponding to and having the same size as one of the orthopedic devices in the first plurality, the joint engaging members of the second plurality of orthopedic devices comprising a polymeric material different than the polymeric material used to make the first plurality of orthopedic devices.

14. An orthopedic kit as defined in claim 13, wherein the joint engaging member of each of the second plurality of orthopedic devices is comprised of an ultrahigh molecular weight polyethylene.

\* \* \* \* \*